US010912855B2

(12) United States Patent
Webster et al.

(10) Patent No.: US 10,912,855 B2
(45) Date of Patent: Feb. 9, 2021

(54) SCENT DISPENSER/ABSORBER AND METHOD USING SAME

(71) Applicant: NOVIA PRODUCTS, LLC, Portland, ME (US)

(72) Inventors: William Webster, Portland, ME (US); Randy M. Oliver, Limerick, ME (US); David Gallant, Newfield, ME (US)

(73) Assignee: NOVIA PRODUCTS, LLC, Portland, ME (US)

( * ) Notice: Subject to any disclaimer, the term of this patent is extended or adjusted under 35 U.S.C. 154(b) by 149 days.

(21) Appl. No.: 16/178,554

(22) Filed: Nov. 1, 2018

(65) Prior Publication Data
US 2019/0125916 A1 May 2, 2019

Related U.S. Application Data

(60) Provisional application No. 62/581,010, filed on Nov. 2, 2017.

(51) Int. Cl.
A61L 9/12 (2006.01)
A61L 9/014 (2006.01)
(Continued)

(52) U.S. Cl.
CPC .............. A61L 9/12 (2013.01); A61L 9/014 (2013.01); A01K 27/007 (2013.01);
(Continued)

(58) Field of Classification Search
None
See application file for complete search history.

(56) References Cited

U.S. PATENT DOCUMENTS 1,481,325 A 1/1924 Le Gris
1,924,823 A 8/1933 Willi
(Continued)

FOREIGN PATENT DOCUMENTS

EP 0335669 6/1993
EP 0691113 1/1996

OTHER PUBLICATIONS

"8-in-1 Excel Calm Quil Natural Calming Charm Collar for Small Dogs"—Amazon.com pp. 1-2. The Wayback Machine—accessed on May 23, 2020 https://web.archive.org/web/20100823084008/ https://www.amazon.com/Excel-Natural-Calming-Charm-Collar/dp/ B00251C8TS (Year: 2010).*
(Continued)

Primary Examiner — Jelitza M Perez
(74) Attorney, Agent, or Firm — Lewis Roca Rothgerber Christie LLP

(57) ABSTRACT

A scent dispenser/absorber includes a pair of cylindrical housing members arranged coaxially about a common longitudinal axis such that the inner housing member is rotatably received in an interior chamber of the outer housing member. Each housing member has a peripheral sidewall provided with a set of radially extending apertures. A scent cartridge is removably disposed within an interior chamber of the inner housing member to absorb undesirable odors, or to emit desirable scents. By manually controlling the relative rotational positions of the housing members, a user can align or misalign the two sets of apertures, thereby enabling or disabling the transfer of scents or odors between the scent cartridge and the surrounding environment.

24 Claims, 4 Drawing Sheets

(51) Int. Cl.
*A01K 27/00* (2006.01)
*A01M 31/00* (2006.01)

(52) U.S. Cl.
CPC ...... *A01M 31/008* (2013.01); *A61L 2209/133* (2013.01); *A61L 2209/15* (2013.01)

(56) References Cited

U.S. PATENT DOCUMENTS

| | | |
|---|---|---|
| 2,234,062 A | 3/1941 | Roberts |
| 2,763,395 A | 9/1956 | Meek |
| 3,873,281 A | 3/1975 | Himes et al. |
| 3,888,416 A | 6/1975 | Lin |
| D250,801 S | 1/1979 | Bergen et al. |
| 4,137,200 A | 1/1979 | Wood et al. |
| 4,146,566 A | 3/1979 | Gaiser |
| 4,200,229 A | 4/1980 | Spector |
| 4,327,056 A | 4/1982 | Gaiser |
| 4,549,693 A | 10/1985 | Barlics |
| 4,869,407 A | 9/1989 | Booth, Jr. et al. |
| 4,957,810 A | 9/1990 | Eleouet et al. |
| 5,064,653 A | 11/1991 | Sessions et al. |
| D351,650 S | 10/1994 | Vavra |
| 5,388,762 A | 2/1995 | Bryson, Sr. |
| D372,770 S | 8/1996 | Foreman |
| 5,610,674 A | 3/1997 | Martin |
| D387,734 S | 12/1997 | Hawkins, Jr. et al. |
| 5,837,377 A | 11/1998 | Sheu et al. |
| 5,880,216 A | 3/1999 | Tanihara et al. |
| 5,898,475 A | 4/1999 | Martin |
| 5,973,221 A | 10/1999 | Collyer et al. |
| D422,481 S | 4/2000 | Bertani |
| 6,277,401 B1 | 8/2001 | Bello et al. |
| 6,617,014 B1 | 9/2003 | Thomson |
| D493,875 S | 8/2004 | Groene et al. |
| 6,889,870 B2 | 5/2005 | De Laforcade |
| 6,991,848 B2 | 1/2006 | Thomson |
| 6,997,355 B2 | 2/2006 | Duquet et al. |
| 7,048,966 B2 | 5/2006 | Thomson |
| D550,840 S | 9/2007 | Anderson et al. |
| D568,715 S | 5/2008 | Gustafson et al. |
| D575,711 S | 8/2008 | Johannsen |
| D676,551 S | 2/2013 | Desai et al. |
| 8,544,766 B2 | 10/2013 | Webster et al. |
| D710,699 S | 8/2014 | Phelps |
| D791,426 S | 7/2017 | Petersen |
| D794,765 S | 8/2017 | Brandenburg et al. |
| D830,530 S | 10/2018 | Webster et al. |
| 2002/0018884 A1 | 2/2002 | Thomson |
| 2002/0113909 A1 | 8/2002 | Sherwood |
| 2004/0144811 A1 | 7/2004 | Pennaneac'H |
| 2006/0216492 A1 | 9/2006 | Thomson |
| 2007/0187524 A1 | 8/2007 | Sherwood |
| 2007/0224232 A1 | 9/2007 | Sherwood |
| 2010/0314465 A1* | 12/2010 | Webster .............. A61L 9/12 239/34 |
| 2011/0147478 A1 | 6/2011 | Bernstein |
| 2013/0206861 A1 | 8/2013 | Webster et al. |
| 2017/0312380 A1 | 11/2017 | Webster et al. |

OTHER PUBLICATIONS

U.S. Appl. No. 29/678,613, filed Jan. 30, 2019.
U.S. Appl. No. 16/401,043, filed May 1, 2019.
U.S. Appl. No. 62/480,948, filed Apr. 30, 2017.
www.scentair.com/products/index.php?subSectionID=2.
ScentWave SWD-1000 Technical Specifications.
ScentStream SXD-5020 Technical Specifications.
ScentPOP Technical Specifications.

* cited by examiner

SCENT DISPENSER/ABSORBER AND METHOD USING SAME

CROSS-REFERENCE TO RELATED APPLICATIONS

The present application claims the benefit of U.S. Provisional Patent Application Ser. No. 62/581,010, filed Nov. 2, 2017, which is incorporated by reference herein in its entirety.

FIELD OF INVENTION

The disclosed subject matter relates to dispensers of scents into the environment and/or absorbers of odors or materials from the environment.

BACKGROUND OF THE INVENTION

Various forms of dispensers of scents into the environment, such as household or other building interior environments, or devices for removing odors or materials from such environments, are known in the art. Many of these dispensers and/or devices have a multi-component design requiring them to be assembled with the use of independent fasteners and/or tools. An object of the present invention is to provide a versatile scent-dispensing/absorbing apparatus that is efficient and effective in use, while maintaining simplicity and economics of manufacture and operation.

SUMMARY OF THE INVENTION

A scent-dispensing/absorbing apparatus includes a pair of cylindrical housing members arranged coaxially about a common longitudinal axis such that the housing members can be rotated relative to one another about their common longitudinal axis. An inner one of the housing members has a cylindrical sidewall surrounding an interior chamber containing scent means adapted to perform either a scent-absorbing function or a scent-emitting function. The sidewall of the inner housing member has a set of apertures extending through it in a radial direction. The other or outer housing member includes a sidewall surrounding an interior chamber in which the inner housing member is removably received. The sidewall of the outer housing member has its own set of apertures extending through it in a radial direction. The two sets of apertures are arranged such that they can be put into or out of alignment in response to the relative rotation of the inner and outer housing members. When the two sets of apertures are aligned, the apparatus allows (i) desirable scents to flow from the scent means to the environment or (ii) undesirable odors in the environment to flow into the scent means, where they can be absorbed. When the two sets of apertures are not aligned, the scent means is isolated from the environment, whereby undesirable odors and desirable scents are prevented from flowing into or out of the apparatus.

The scent-dispensing/absorbing apparatus can be combined with a pet collar. Such a combination can be used in connection with a method for calming a dog, for instance, by loading the scent means with a canine pheromone.

BRIEF DESCRIPTION OF THE DRAWINGS

For a better understanding of the present invention, reference is made to the following detailed description of an exemplary embodiment considered in conjunction with the accompanying drawings, in which like structures are referred to by the like reference numerals throughout the several views, and in which.

DETAILED DESCRIPTION OF THE INVENTION

Figure 1:
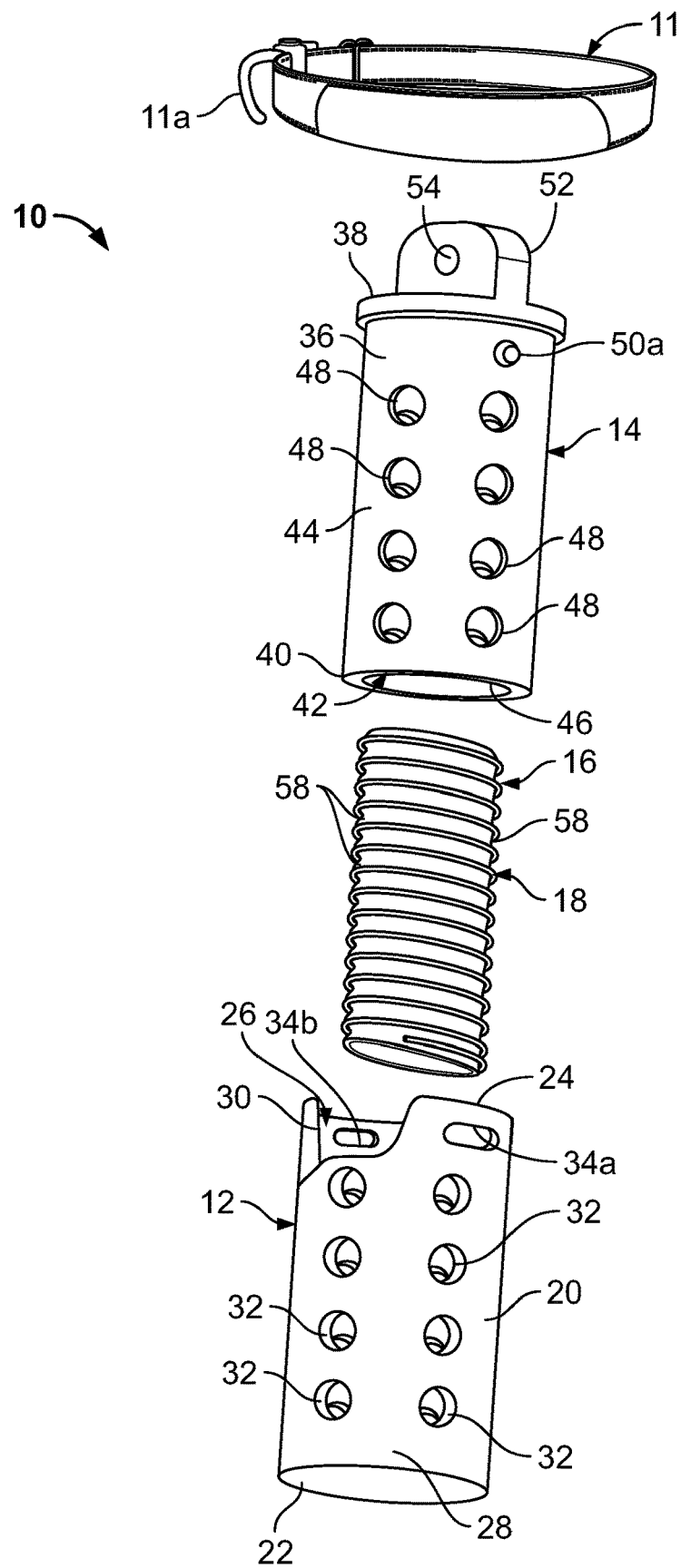
FIG. 1 is an exploded perspective view of a scent dispenser and dog collar which have been combined in accordance with an exemplary embodiment of the present invention, a portion of the scent dispenser being broken away to facilitate consideration and discussion.
Figure 2:
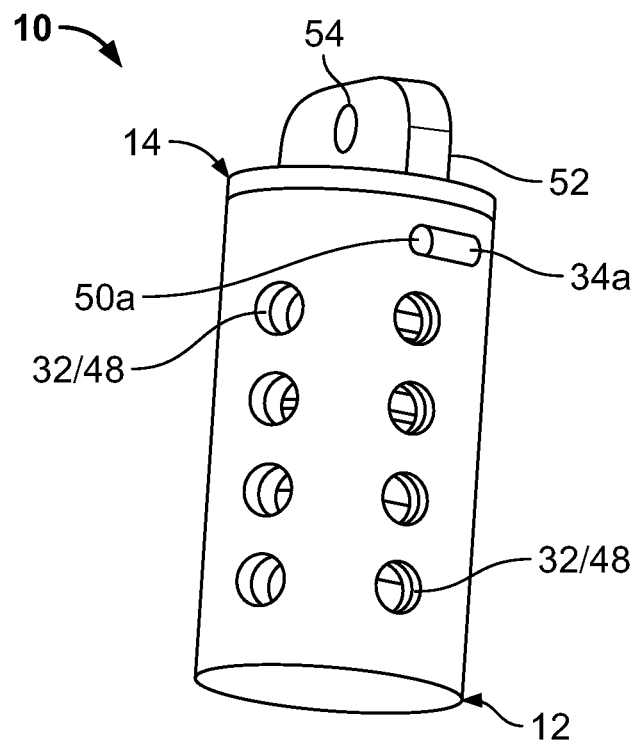
FIG. 2 is a perspective view of the scent dispenser of FIG. 1, which is shown assembled and in an open position.
Figure 3:
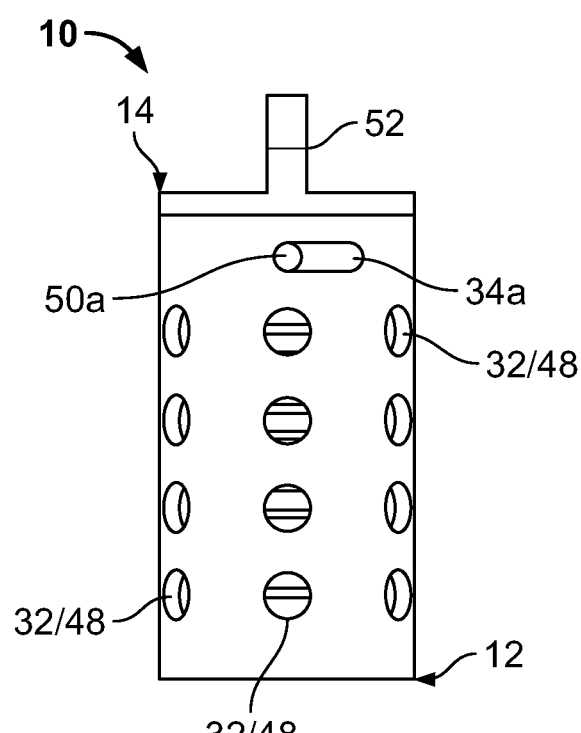
FIG. 3 is a side elevational view of the scent dispenser of FIGS. 1 and 2.
Figure 4:
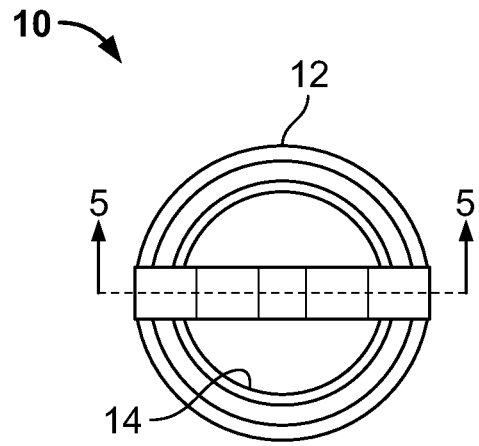
FIG. 4 is a top plan view of the scent dispenser of FIGS. 1-3, the scent dispenser having been rotated 90° from the position shown in FIG. 3.
Figure 5:
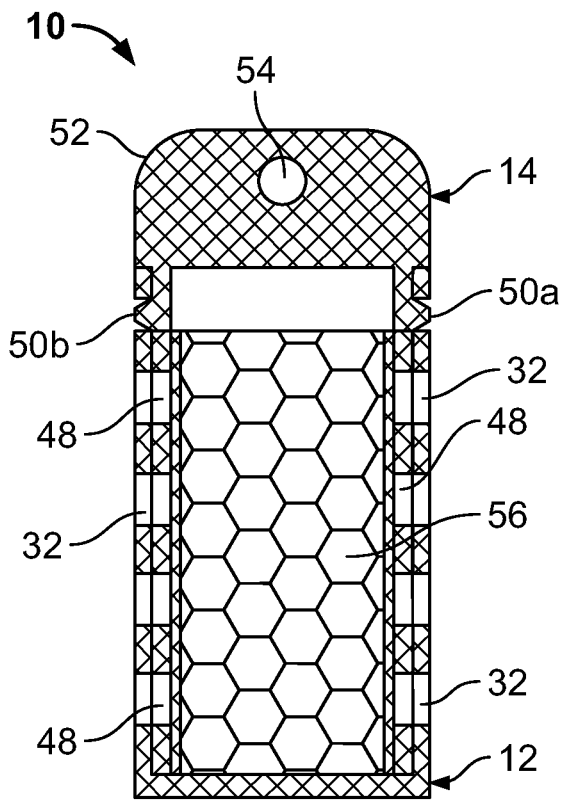
FIG. 5 is a cross-sectional view of the scent dispenser of FIG. 4 taken along the section line V-V of FIG. 4 and looking in the direction of the arrows.
Figure 6:
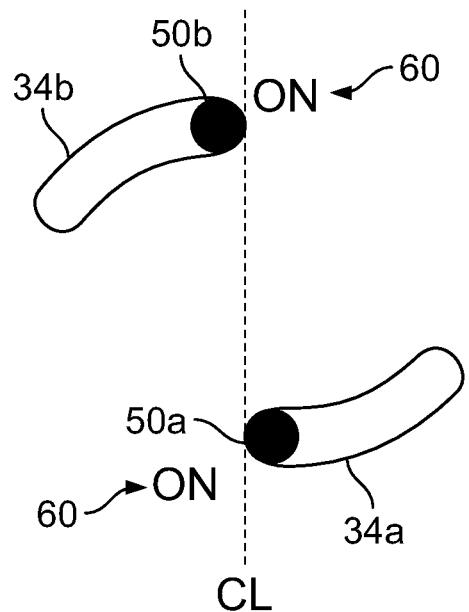
FIG. 6 is a schematic illustration showing pin/slot relationships when the scent dispenser of FIGS. 1-5 is in its open position.
Figure 7:
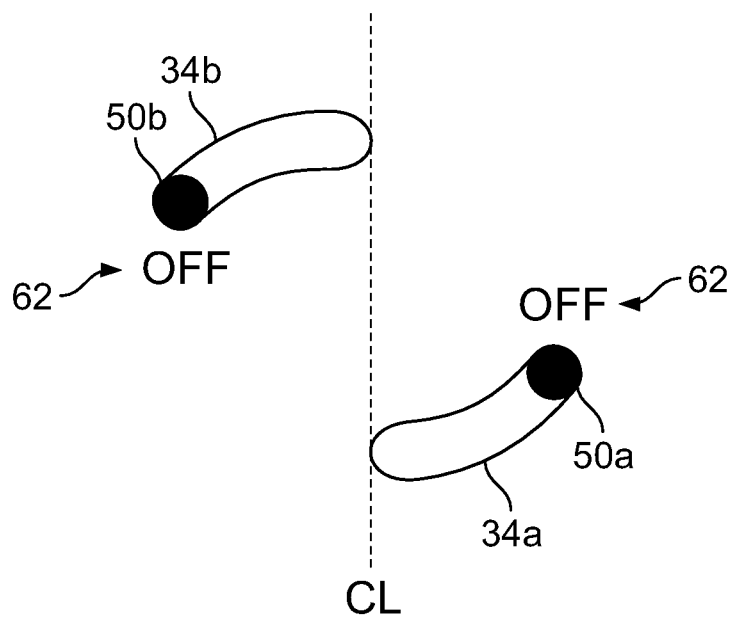
FIG. 7 is a schematic illustration showing pin/slot relationships when the scent dispenser of FIGS. 1-5 is in its closed position.

FIG. 1 presents a scent dispenser 10 and its component parts according to an exemplary embodiment in which the scent dispenser 10 is adapted for attachment to a dog collar 11. FIGS. 1 and 2 are perspective views of the scent dispenser 10 that illustrate relationships among its various elements. However, consistent with the nature of perspective views, some elements of the scent dispenser 10 described herein are not visible in those figures. All such elements of the scent dispenser 10 are discussed further in relation to FIGS. 3-7, which present elevational, plan, cross-sectional or schematic views of certain component parts of the scent dispenser 10. Terms indicating position, orientation or direction of motion are used throughout the discussion of FIGS. 3-7 in relation to the component parts and are consistent with the orientation of the parts shown in FIGS. 1 and 2, unless otherwise expressly noted. Such terms are used for the purpose of facilitating discussion, and not to limit the embodiment to the particular terms described herein or to limit physical orientation in actual use to any particular coordinate system (e.g., horizontal, vertical and front, back and side), during actual use of the scent dispenser 10 in combination with the dog collar 11 or otherwise.

With the foregoing prefatory comments in mind, and with particular reference to FIG. 1, the scent dispenser 10 mentioned in the preceding paragraph includes the following four components: a barrel-like cap 12, which forms an outer housing member for the scent dispenser 10; a cylindrical top 14, which forms an inner housing member for the scent dispenser 10; a scent cartridge 16; and a retaining spring 18, which is associated with the scent cartridge 16 for a purpose/function to be described hereinafter. Further descriptions of the aforementioned components will follow, while making reference to FIGS. 2-7, as well as to FIG. 1.

The cap 12 or other housing member includes a body 20, which has a cylindrical shape; a closed end 22; and an open end 24, which leads to an interior chamber 26. The body 20 of the cap 12 includes a cylindrical outer sidewall 28 of a first diameter and a cylindrical inner sidewall 30 of a second diameter, which is less than the first diameter. A plurality of round diffusion ports 32 is provided in the body 20 of the cap 12, each of the diffusion ports 32 extending from the outer sidewall 28 to the inner sidewall 30 for a purpose/function to be described hereinafter. The diffusion ports 32 are arranged in rows and columns for a purpose/function to be described hereinafter. The body 20 of the cap 12 is also provided with a pair of elongated index slots 34a, 34b, each of which extends from the outer sidewall 28 to the inner sidewall 30 for a purpose/function to be described hereinafter. The index slots 34a, 34b are arranged on diametrically opposed portions of the body 20 of the cap 12 adjacent to the open end 24 thereof. The cap 12 can be made from any suitable material, but is preferably made from a plastic material such as poly-vinyl chloride and the like.

Like the cap 12, the top or inner housing member 14 can be made from any suitable material, but is preferably made from a plastic material such as poly-vinyl chloride and the like. The top 14 includes a body 36, which has a cylindrical shape; a closed end 38; and an open end 40, which leads to an interior chamber 42. The body 36 of the top 14 includes a cylindrical outer sidewall 44 of a third diameter, which is substantially the same as, but not greater than, the diameter of the inner sidewall 30 of the cap 12 (i.e., the aforesaid second diameter), and a cylindrical inner sidewall 46 of a fourth diameter, which is less than the third diameter.

A plurality of round diffusion ports 48 is provided in the body 36 of the top 14, each of the diffusion ports 48 extending from the outer sidewall 44 to the inner sidewall 46 for a purpose/function to be described hereinafter. Like the diffusion ports 32, the diffusion ports 48 are arranged in rows and columns whose spacing is the same as the spacing between the rows and columns formed by the diffusion ports 32 of the cap 12. As can be seen with particular reference to FIG. 5, the size and shape of the diffusion ports 48 match the size and shape of the diffusion ports 32. The relationship of the shape, size and arrangement of the diffusion ports 48, on the one hand, and the diffusion ports 32, on the other hand, will be described in greater detail hereinafter.

The body 36 of the top 14 is also provided with a pair of tapered index pins 50a, 50b, the index pin 50a being positioned on one side of the body 36 adjacent the closed end 38 and the index pin 50b being positioned on a diametrically opposed side of the body adjacent the closed end 38. Each of the index pins 50a, 50b has its widest portion adjacent the outer sidewall 44 from which both of the pins 50a, 50b extend in a radially outward direction for a purpose/function to be described hereinafter. The remote ends of the index pins 50a, 50b (i.e., the narrow-most portions of the index pins 50a, 50b) are resiliently deflectable for a purpose/function to be described hereinafter.

The closed end 38 of the top 14 includes a gripping tab 52 having an aperture 54, which extends through the gripping tab 52. The aperture 54 is sized to receive a clip or hook 11a on the dog collar 11 for removably attaching the scent dispenser 10 to the dog collar 11. Of course, any other known type of attachment mechanism, such as a string, cord, clasp or the like, could be employed to attach the scent dispenser 10 to the dog collar 11.

Still referring to FIG. 1, the scent cartridge 16 includes a core 56 that can absorb and/or adsorb a volatile scented substance and allows the ready passage of air through the core 56. In some embodiments, such as the illustrated embodiment, the scent cartridge 16 includes a frame, such as the spring 18, that provides structural support to the core 56 and helps to maintain its shape. In some embodiments, such as the illustrated embodiment of FIG. 1, the frame (i.e., spring 18) has open gaps 58 through which air may flow. In the illustrated embodiment of FIG. 1, the core 56 of the scent cartridge 16 is loaded with a liquid form of canine pheromone, either before or after the scent dispenser 10 is removably attached to, or retrofitted to, the dog collar 11 using the clip or hook 11a, which is sized and shaped such that it passes through the aperture 54 in the gripping tab 52 of the top 14. The particular pheromone would be selected so as to have a calming effect on the dog. Because the scent dispenser 10 would be hung directly below the dog's nose, it would be immediately effective when in its open position as depicted in FIGS. 1-6. To prolong its useful operating life, the scent dispenser 10 can be put into its closed position (see FIG. 7) when, for instance, the dog is no longer exposed to a stressful situation.

Because the scent dispenser 10 can be disassembled by removing the top 14 from the cap 12, the scent cartridge 16 can be accessed and refilled with the same or a different scent material. By way of further example only, the core 56 could contain a suitable amount of any other desired volatile substance, such as those used (i) in perfumes, (ii) for attracting game, (iii) as diet aids, (iv) for aroma therapy, (v) for medical applications, (vi) or for any other uses which are known or may become known. In some embodiments, the core 56 is arranged such that the scented substance may be added directly to the core 56 to replenish or change the scent.

By way of further example, the core 56 of the scent cartridge 16 may be made of any material that can carry and release volatile scented substances. In some embodiments of the invention, the core 56 is made of an absorbent fibrous material or closed cell foam having air passages penetrating therethrough. In other embodiments of the invention, the core 56 is made of an open-cell foam that presents an appreciable ratio of surface area to volume of foam, with higher ratios typically being preferred. In such embodiments of the invention, the foam may be a hydrophilic foam or have a hydrophilic material exposed at the surfaces of the cells. In some such embodiments, the core 56 comprises an open-cell foam composite made of substantially hydrophobic foam to provide structure to the composite and substantially hydrophilic foam exposed at the surfaces of the cells. An example of such foam is described in U.S. Pat. No. 6,617,014, whose disclosure is incorporated herein by reference in its entirety.

In other embodiments, for example, the core 56 of the scent cartridge 16 may comprise a nonwoven fibrous material substrate coated with a coating material, such as a substantially hydrophilic foam coating which is exposed at the surface and in interstitial spaces within the nonwoven fibrous material. The interstitial spaces within the nonwoven fibrous material form air passages penetrating through the core 56 to allow air to flow therethrough. Suitable nonwoven fibrous materials include, for example without limitation, cotton, felt, silk, or combinations thereof. As will be recognized by persons of ordinary skill in the relevant art, such embodiments would be useful, for example, when the volatile scented substances applied to the core 56 are of the types that may react with and degrade some hydrophobic foams which are suitable for forming the core 56 (see, e.g., U.S. Pat. No. 8,544,766, which is incorporated herein by reference in its entirety).

While not intending to be limiting, one possible embodiment of a process for producing the core 56 having a nonwoven fibrous substrate provided with a coating material, such as a substantially hydrophilic foam, will now be described. Where the substantially hydrophilic foam is produced by a process involving the provision of a prepolymer emulsion and then polymerizing or curing the emulsion, as will be understood by persons of ordinary skill in the relevant art, the core 56 may be produced by contacting the substrate of nonwoven fibrous material with the prepolymer emulsion and then polymerizing or curing the emulsion. By way of example, the substrate can be dipped or immersed in the prepolymer emulsion, which can also be applied by brushing, spraying or otherwise coating onto the substrate. By way of further example, and without limitation, the substrate of nonwoven fibrous material may be provided as a sheet or block and then sprayed with the prepolymer emulsion, followed by polymerization or curing of the emulsion to form the substantially hydrophilic foam on the nonwoven fibrous substrate. The substrate can then be cut into appropriately sized pieces to produce the core 56 or multiple appropriately-sized cores having a variety of shapes, such as cylindrical or a block with a square or rectangular cross-sectional shape.

To assemble the scent dispenser 10, the scent cartridge 16, including its supporting spring 18, is inserted into the interior chamber 42 of the top 14. After setting the top 14 on the cap 12 and aligning the index pins 50a, 50b on the top 14 with the index slots 34a, 34b in the cap 12, the top 14 is pushed into the interior chamber 26 of the cap 12 until each of the index pins 50a, 50b deflects and seats in a corresponding one of the index slots 34a, 34b, thereby mating the top 14 with the cap 12 in such a manner that the cap 12 and the top 14 are rotatable relative to each other. While the taper on the index pins 50a, 50b facilitates their insertion into the index slots 34a, 34b, respectively, the gripping tab 52 facilitates the rotation of the top 14 relative to the cap 12 by providing a finger hold for a user or assembly person.

In the relative positions depicted in FIGS. 1-6, the index pin 50a is in abutment with one end of the index slot 34a, while the index pin 50b is in abutment with one end of the index slot 34b, thereby aligning the diffusion ports 32 in the cap or outer housing member 12 with the diffusion ports 48 in the top or inner housing member 14. In the condition illustrated in FIGS. 1-6, the scent dispenser 10 is in its open position, in which, for example, it is adapted to dispense a scent into the surrounding environment. The cap or outer housing member 12 may be provided with indicia 60, such as the word or words "ON", indicating that the scent dispenser 10 is in its open or on position.

The scent dispenser 10 can be put into a closed position by manually grabbing the gripping tab 52 and rotating the top 14 relative to the cap 12 until the index pin 50a abuts an opposite end of the index slot 34a and the index pin 50b abuts an opposite end of the index slot 34b (see FIG. 7), whereby the diffusion ports 32 in the cap 12 are not aligned with the diffusion ports 48 in the top 14. In such a condition (not shown in FIGS. 1-5), the diffusion ports 32 in the cap or outer housing member 12 are completely blocked by the outer sidewall of the top or inner housing member 14, thereby preventing, for example, the diffusion of any scent from the scent dispenser 10. The cap or outer housing member 12 may be provided with indicia 62, such as the word or words "OFF", indicating that the scent dispenser 10 is in the closed or off position.

While the present invention has been described with reference to a specific embodiment thereof, it should be understood by those skilled in the art that various changes may be made and equivalents may be substituted without departing from the true spirit and scope of the invention. In addition, many modifications may be made to the embodiment described herein to adapt it to a particular situation, use or application without departing from the overall objective, spirit and/or scope of the present invention. By way of example, and without limitation, the scent dispenser 10 can be converted into a scent absorber by omitting any scent material from the scent cartridge 16. When used in combination with the dog collar 11, the converted scent absorber could function to remove undesirable odors emanating from the dog or the dog's environment.

We claim:

1. An apparatus adapted to dispense and/or absorb scents, comprising:

an outer housing member having an open end, a closed end, and a cylindrical sidewall extending between said open and closed ends of said outer housing member and delimiting an interior chamber having an imaginary longitudinal axis passing therethrough, said sidewall of said outer housing member having a first plurality of circumferentially and longitudinally spaced apertures and at least one circumferentially elongated slot; and an inner housing member received within said interior chamber of said outer housing member such that said inner and outer housing members are arranged coaxially about said imaginary longitudinal axis and such that said inner housing member is rotatable relative to said outer housing member about said imaginary longitudinal axis between a first rotational position and a second rotational position, said inner housing member having an open end positioned within said interior chamber of said outer housing member, a closed end protruding from said open end of said outer housing member, and a cylindrical sidewall extending between said open and closed ends of said inner housing member and delimiting an interior chamber sized and shaped to contain a scent cartridge adapted to perform a scent-emitting function or a scent-absorbing function, said sidewall of said inner housing member having a second plurality of circumferentially and longitudinally spaced apertures and at least one pin projecting radially outward from said sidewall of said inner housing member, each of said at least one pin being movably received in a respective one of said at least one slot to thereby longitudinally align at least some of said first plurality of apertures with at least some of said second plurality of apertures, said first and second pluralities of apertures being arranged in said sidewalls of said outer and inner housing members, respectively, such that said at least some of said first plurality of apertures are radially aligned with said at least some of said second plurality of apertures when said inner housing member is in said first rotational position relative to said outer housing member, thereby allowing scent to pass through said outer and inner housing members to or from said interior chamber of said inner housing member, and such that said first and second pluralities of apertures are not radially aligned when said inner housing member is in said second rotational position relative to said outer housing member, thereby preventing scent from passing through said outer and inner housing members to or from said interior chamber of said inner housing member.

2. An apparatus according to claim 1, wherein each of said at least one slot has a first end and a second end; wherein each of said at least one pin abuts said first end of a respective one of said at least one slot when said inner housing member is in said first rotational position relative to said outer housing member; and wherein each of said at least one pin abuts said second end of a respective one of said at least one slot when said inner housing member is in said second rotational position relative to said outer housing member.

3. An apparatus according to claim 2, wherein said at least one pin includes a pair of pins and said at least one slot includes a pair of slots, one slot of said pair of slots receiving one pin of said pair of pins and the other slot of said pair of slots receiving the other pin of said pair of pins.

4. An apparatus according to claim 3, wherein said one pin and said other pin are arranged on diametrically opposed sides of said sidewall of said inner housing member; and
wherein said one slot and said other slot are arranged on diametrically opposed sides of said sidewall of said outer housing member.

5. An apparatus according to claim 4, wherein said inner housing member is slidably and removably insertable within said interior chamber of said outer housing member.

6. An apparatus according to claim 5, wherein said one pin and said other pin are resiliently deflectable in response to their engagement with said sidewall of said outer housing member during insertion of said inner housing member into said outer housing member.

7. An apparatus according to claim 6, wherein said one pin and said other pin are tapered from a wide portion adjacent said sidewall of said inner housing member to a narrow portion remote from said sidewall of said inner housing member to thereby facilitate insertion of said inner housing member into said outer housing member.

8. An apparatus according to claim 1, further comprising a scent cartridge received within said interior chamber of said inner housing member.

9. An apparatus according to claim 8, wherein said scent cartridge is removably received within said interior chamber of said inner housing member.

10. An apparatus according to claim 9, wherein said scent cartridge is removable from said interior chamber of said inner housing member through said open end of said inner housing member.

11. An apparatus according to claim 10, wherein said scent cartridge is insertable within said interior chamber of said inner housing member through said open end of said inner housing member.

12. An apparatus according to claim 8, wherein said scent cartridge contains a volatile scented substance, whereby said apparatus functions as a scent dispenser when said inner housing member is in said first rotational position relative to said outer housing member.

13. An apparatus according to claim 12, wherein said outer housing member includes first indicia indicating a scent-dispensing condition of said apparatus and second indicia indicating a non-scent dispensing condition of said apparatus.

14. An apparatus according to claim 12, wherein said volatile scented substance is a liquid form of canine pheromone.

15. An apparatus according to claim 14, wherein said apparatus is removably attachable to a dog collar.

16. An apparatus according to claim 1, wherein said inner housing member includes a tab projecting from said closed end of said inner housing member, said tab being sized and shaped so as to be manually grippable by a user for the purpose of rotating said inner housing member relative to said outer housing member.

17. An apparatus according to claim 16, wherein said tab is attachable to a dog collar.

18. An apparatus according to claim 1, wherein said open end of said inner housing member is proximate said closed end of said outer housing member.

19. An apparatus according to claim 18, wherein said sidewall of said inner housing member is proximate said sidewall of said outer housing member.

20. An apparatus according to claim 19, wherein each of said first plurality of apertures extends through said sidewall of said outer housing member in a generally radial direction substantially perpendicular to said imaginary longitudinal axis; and wherein each of said second plurality of apertures extends through said sidewall of said inner housing member in a generally radial direction substantially perpendicular to said imaginary longitudinal axis.

21. An apparatus according to claim 20, wherein each of said at least one slot extends through said sidewall of said outer housing member in a generally radial direction.

22. An apparatus according to claim 8, wherein said scent cartridge is void of any scented substance upon its initial insertion into said inner housing member, whereby said apparatus functions as a scent absorber when said inner housing member is in said first rotational position relative to said outer housing member.

23. In combination: a dog collar; and a scent-dispensing apparatus which comprises an outer housing member having an open end, a closed end, and a cylindrical sidewall extending between said open and closed ends of said outer housing member and delimiting an interior chamber having an imaginary longitudinal axis passing therethrough, said sidewall of said outer housing member having a first plurality of circumferentially and longitudinally spaced apertures and at least one circumferentially elongated slot, and an inner housing member received within said interior chamber of said outer housing member such that said inner and outer housing members are arranged coaxially about said imaginary longitudinal axis and such that said inner housing member is rotatable relative to said outer housing member about said imaginary longitudinal axis between a first rotational position and a second rotational position, said inner housing member having an open end positioned within said interior chamber of said outer housing member, a closed end protruding from said open end of said outer housing member, and a cylindrical sidewall extending between said open and closed ends of said inner housing member and delimiting an interior chamber containing a scent cartridge provided with a liquid form of canine pheromone, said sidewall of said inner housing member having a second plurality of circumferentially and longitudinally spaced apertures and at least one pin projecting radially outward from said sidewall of said inner housing member, each of said at least one pin being movably received in a respective one of said at least one slot to thereby longitudinally align at least some of said first plurality of apertures with at least some of said second plurality of apertures, said first and second pluralities of apertures being arranged in said sidewalls of said outer and inner housing members, respectively, such that said at least some of said first plurality of apertures are radially aligned with said at least some of said plurality of apertures when said inner housing member is in said first rotational position relative to said outer housing member, thereby allowing scent to pass through said inner and outer housing members from said scent cartridge, and such that said first and second pluralities of apertures are not radially aligned when said inner housing member is in said second rotational position relative to said outer housing member, thereby preventing scent from passing through said inner and outer housing members from said scent cartridge.

24. A method of calming a canine animal using the combination of claim 23, said method comprising the steps of attaching said collar to a canine animal; and rotating said inner housing member relative to said outer housing member until said inner housing member is in said first rotational position.

\* \* \* \* \*